(12) United States Patent
Kohler et al.

(10) Patent No.: US 10,470,806 B2
(45) Date of Patent: Nov. 12, 2019

(54) MAXILLOMANDIBULAR FIXATION DEVICES

(71) Applicant: KLS-Martin, L.P., Jacksonville, FL (US)

(72) Inventors: Klaus Kohler, Muhlheim (DE); Jennifer Pinto, Jacksonville, FL (US); Thomas S. Johnston, Jr., Jacksonville, FL (US); Francis A. Papay, Cleveland, OH (US)

(73) Assignees: KLS-MARTIN, L.P., Jacksonville, FL (US); THE CLEVELAND CLINIC FOUNDATION, Cleveland, OH (US)

( * ) Notice: Subject to any disclaimer, the term of this patent is extended or adjusted under 35 U.S.C. 154(b) by 56 days.

(21) Appl. No.: 15/891,144

(22) Filed: Feb. 7, 2018

(65) Prior Publication Data
US 2018/0221069 A1    Aug. 9, 2018

Related U.S. Application Data

(60) Provisional application No. 62/455,957, filed on Feb. 7, 2017.

(51) Int. Cl.
    *A61B 17/80* (2006.01)
(52) U.S. Cl.
    CPC ............... *A61B 17/8071* (2013.01)
(58) Field of Classification Search
    CPC .......................................... A61B 17/80–809
    USPC ................... 606/70, 71, 280–299, 903, 904
    See application file for complete search history.

(56) References Cited

U.S. PATENT DOCUMENTS

| | | | | |
|---|---|---|---|---|
| 6,129,728 A * | 10/2000 | Schumacher | ...... | A61B 17/8047 606/104 |
| 6,325,803 B1 * | 12/2001 | Schumacher | ...... | A61B 17/8047 606/104 |
| 6,827,574 B2 * | 12/2004 | Payton | ...... | A61C 7/00 433/173 |
| 8,118,850 B2 | 2/2012 | Marcus | | |
| 8,282,635 B1 * | 10/2012 | Amato | ...... | G09B 23/32 433/18 |
| 8,435,270 B2 * | 5/2013 | Furrer | ...... | A61B 17/151 606/280 |
| 8,784,456 B2 * | 7/2014 | Longepied | ...... | A61B 17/8071 606/284 |
| 8,807,998 B2 * | 8/2014 | Lee | ...... | A61C 7/00 433/18 |
| 8,992,582 B1 * | 3/2015 | Knoepfle | ...... | A61B 17/8028 606/281 |
| 9,066,733 B2 * | 6/2015 | Furrer | ...... | A61B 17/151 |
| 9,220,552 B2 | 12/2015 | Marcus | | |
| 9,247,972 B2 * | 2/2016 | Longepied | ...... | A61B 17/8071 |
| 9,277,948 B2 * | 3/2016 | Furrer | ...... | A61B 17/151 |

(Continued)

*Primary Examiner* — Eric S Gibson
(74) *Attorney, Agent, or Firm* — Thomas C. Saitta

(57) ABSTRACT

A maxillomandibular fixation (MMF) device having an arch bar with a plurality of spaced tabs and gaps, and further having apertured mounting plate members mounted onto the arch bar, each mounting plate member having a slot to receive a tab on the arch bar, whereby the mounting plate members may be repositioned laterally along the arch bar from one tab to another prior to affixing the MMF device to the maxilla or mandible of a patient in order to position the mounting plate members at locations where the underlying tooth root will not be damaged by insertion of a bone screw.

17 Claims, 8 Drawing Sheets

(56) References Cited

U.S. PATENT DOCUMENTS

| | | | |
|---|---|---|---|
| 9,339,279 B2* | 5/2016 | Dubois | A61B 34/10 |
| 9,775,657 B2* | 10/2017 | Bernstein | A61B 17/808 |
| 9,808,297 B2* | 11/2017 | Bernstein | A61B 17/808 |
| 9,820,777 B2* | 11/2017 | Woodburn, Sr. | A61B 17/6433 |
| 2002/0062127 A1* | 5/2002 | Schumacher | A61B 17/8047 606/70 |
| 2005/0203628 A1* | 9/2005 | Elsalanty | A61B 17/8004 623/17.17 |
| 2009/0170050 A1 | 2/2009 | Marcus | |
| 2009/0061377 A1* | 3/2009 | Cope | A61C 7/00 433/18 |
| 2011/0152946 A1* | 6/2011 | Frigg | A61B 17/8071 606/300 |
| 2011/0152951 A1* | 6/2011 | Baker | A61C 7/00 606/328 |
| 2011/0269100 A1* | 11/2011 | Furrer | A61B 17/151 433/72 |
| 2011/0301609 A1* | 12/2011 | Longepied | A61B 17/8071 606/71 |
| 2012/0029574 A1* | 2/2012 | Furrer | A61B 17/151 606/280 |
| 2013/0023938 A1* | 1/2013 | Huebner | A61B 17/8066 606/281 |
| 2013/0090695 A1* | 4/2013 | Bernstein | A61B 17/808 606/281 |
| 2013/0261624 A1* | 10/2013 | Stringer | A61B 17/8066 606/71 |
| 2014/0194878 A1* | 7/2014 | Bernstein | A61B 17/808 606/75 |
| 2015/0265378 A1* | 9/2015 | Furrer | A61B 17/151 700/118 |
| 2015/0297272 A1 | 10/2015 | Ghobadi et al. | |
| 2016/0008042 A1* | 1/2016 | Woodburn, Sr. | A61B 17/6433 606/328 |
| 2016/0331427 A1* | 11/2016 | Waizenegger | A61B 17/176 |
| 2018/0049786 A1* | 2/2018 | Brace | A61B 17/8047 |
| 2018/0125547 A1* | 5/2018 | Bernstein | A61B 17/808 |
| 2018/0221069 A1* | 8/2018 | Kohler | A61B 17/8071 |
| 2018/0360465 A1* | 12/2018 | Furrer | A61B 17/151 |
| 2019/0038414 A1* | 2/2019 | Johnston, Jr. | A61F 2/2803 |

* cited by examiner

MAXILLOMANDIBULAR FIXATION DEVICES

BACKGROUND OF THE INVENTION

This application relates generally to the field of medical apparatuses known as maxillomandibular fixation (MMF) devices, and more particularly to such MMF devices comprising arch bars adapted for fixation to the maxilla or mandible of a patient, each arch bar having hooks, buttons or similar projections, whereby the a pair of arch bars are connected to each other, typically by wire wrapped around and extending between opposing hooks, so as to secure the upper and lower jaws in a closed position.

In some procedures, the MMF arch bars are attached to the teeth using encircling wires. In other procedures, the MMF arch bars are affixed to maxillary or mandibular bone tissue by mechanical fasteners, e.g., bone screws. It is important in these circumstances that the bones screws do not impinge on the roots of the teeth. Early embodiments for such MMF arch bars utilized screw-receiving apertures that were fixed in spaced position along the arch bar, which often resulted in circumstances wherein certain apertures were not available for use because of their location over a tooth root. Later embodiments addressed this by providing apertures on malleable stems such that the location of the aperture could be shifted by bending the stem. Bending stems to adjust the aperture location results in undesirable curvatures out-of-plane and weakens the security of the arch bars once the arch wires are tightened to close the jaw. Other embodiments provide the mounting apertures on mounting assemblies that can be moved along the arch bar and then mechanically fastened to the arch bar by a set screw for example. A problem with this structure is the possibility that the fastening elements may loosen over time.

It is an object of this invention to provide an MMF device that allows for movement or relocation of mounting plate members comprising the screw-receiving apertures along the arch bar to avoid tooth roots, without sacrificing rigidity, strength and fixation.

SUMMARY OF THE INVENTION

Figure 1:
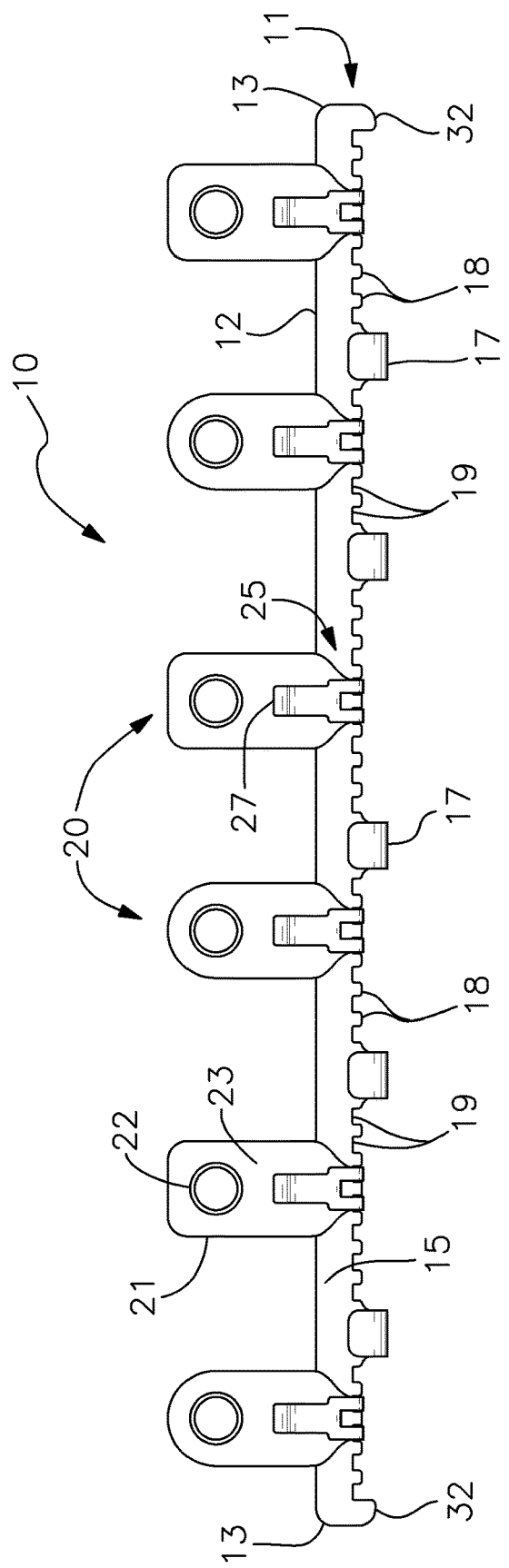
FIG. 1 is a front view of a representative embodiment of the invention.
Figure 2:
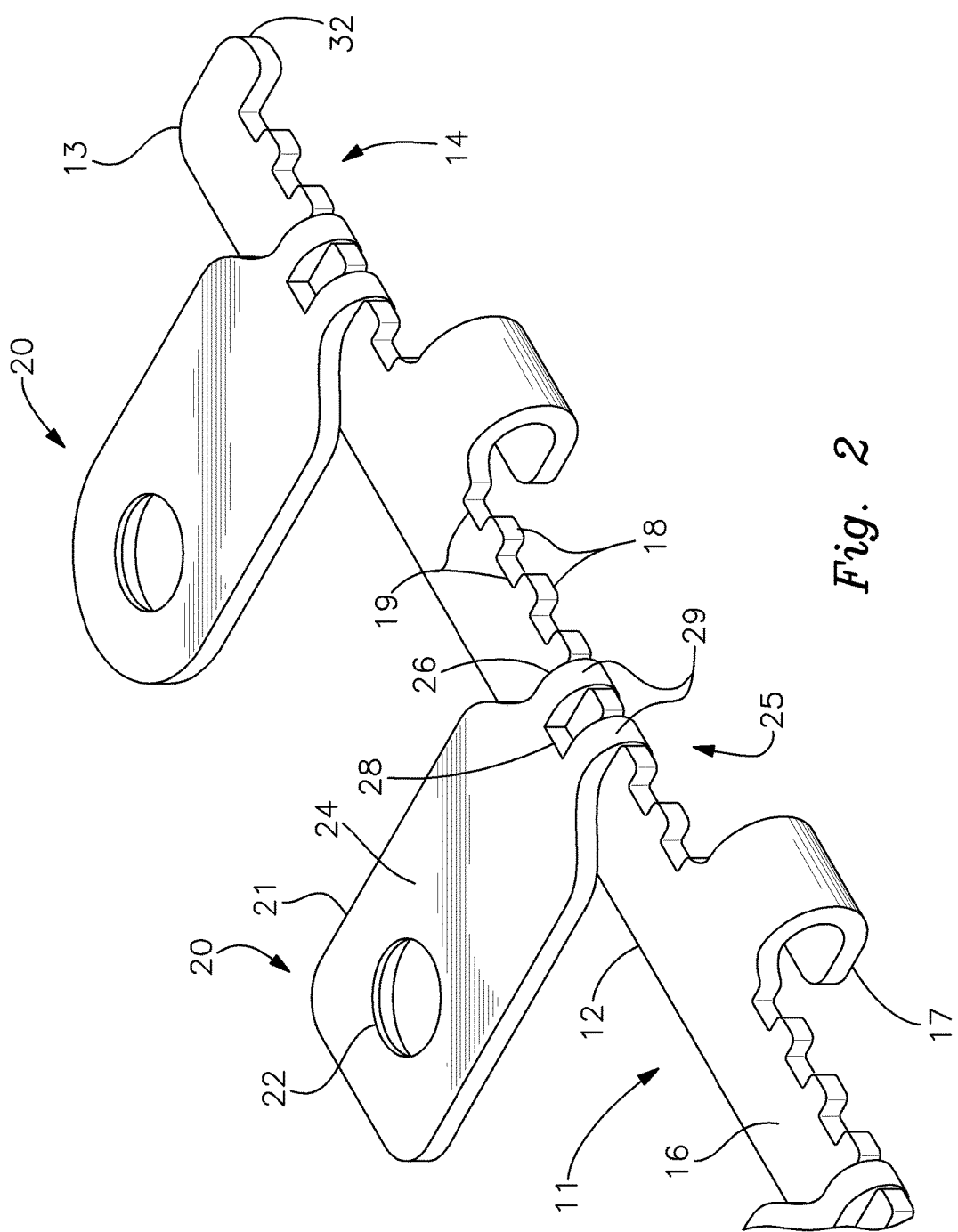
FIG. 2 is a partial rear perspective view of the embodiment of FIG. 1.
Figure 3:
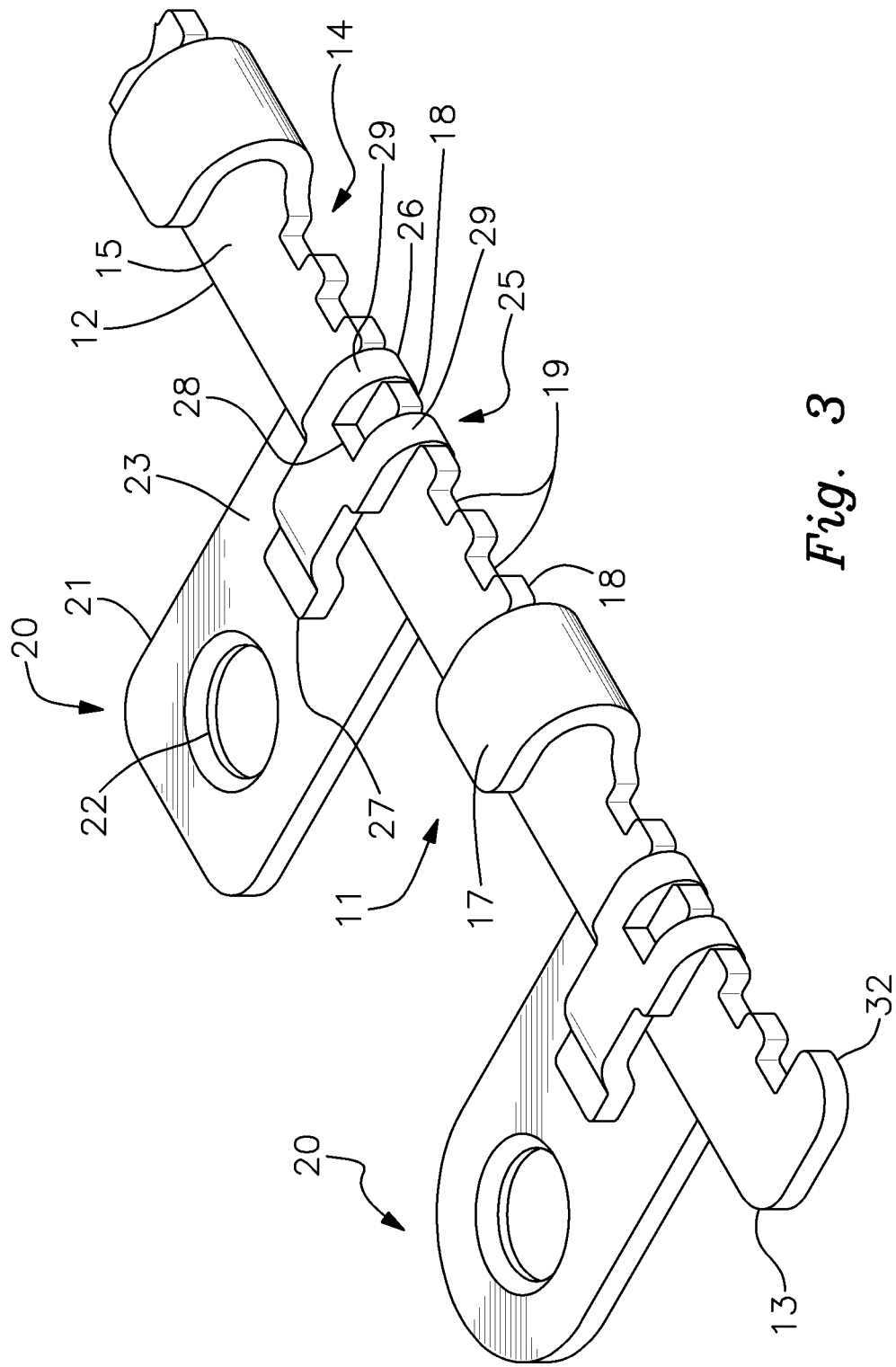
FIG. 3 is a partial front perspective view of the embodiment of FIG. 1.

The invention in various embodiments is a maxillomandibular fixation (MMF) device adapted to be mounted to either a mandible/lower jaw or a maxilla/upper jaw of a patient utilizing mechanical fasteners, the MMF devices to be utilized in pairs with one MMF device positioned on the maxilla and the other MMF device positioned on the mandible. The opposing MMF devices are structured to be fastened or connected to each other, such as by a wire fastener, in a manner that affixes or secures the jaw in a closed position.

Each MMF device comprises an elongated arch bar comprising wire retention projection members, such as hooks or buttons, and a plurality of spaced tabs, teeth, anchors or the like, bounded by gaps, spaces, notches or the like (referred to hereinafter collectively as "gaps") located along one edge of the arch bar, which is the edge of the arch bar that will face the opposing arch bar when in use. The MMF device further comprises a plurality of mounting plate members, each comprising a main body, a screw-receiving aperture and a coupling portion comprising a slotted, curved mid-section, the coupling portion adapted to encircle the arch bar. The slot of the curved midsection is abutted by a pair of leg segments. The slot is sized such an arch bar tab member may be received within the slot, the leg segments of the curved midsection then fitting into the arch bar gaps to either side of the tab member. The coupling portion is sized to provide an open area so that by shifting the mounting plate member in the direction of the slot, the leg segments clear the ends of the tab members, thereby allowing the mounting plate member to be moved laterally along the arch bar to a chosen location where it is shifted in the direction of the screw-receiving aperture to couple the mounting plate member to the desired arch bar tab such that insertion of a bone screw or other mechanical fastener into the screw-receiving aperture will not impact or adversely affect the root of a tooth when the MMF device is mounted to the patient.

DETAILED DESCRIPTION OF THE INVENTION

With reference to the figures, the invention is shown to comprise in various embodiments a maxillomandibular fixation (MMF) device 10 adapted to be mounted to either a mandible/lower jaw or a maxilla/upper jaw of a patient utilizing mechanical fasteners (not shown), such as bone screws or the like. The drawings are provided for illustrative and descriptive purposes as required to enable the invention and are not meant to be limiting as to the scope of the invention. The MMF devices 10 are utilized in pairs, with one MMF device 10 adapted to be positioned on the maxilla and the other MMF device 10 positioned in inverted manner on the mandible. The opposing MMF devices 10 are adapted to be fastened or connected to each other, such as by a wire fastener, in a manner that affixes or secures the jaw in a closed position.

Each MMF device 10 comprises an arch bar 11 comprising an elongated main body 12, ends 13, a front side 15, a rear side 16 and a facing edge 14. The arch bar 11 is illustrated in the drawings as being linear, but in use the main body 12 will be curved to conform to the shape of the mandible or maxilla onto which the arch bar 11 is to be affixed. The arch bar 11 is adapted to be indirectly affixed or attached to the bone of the patient using mechanical fasteners extending through the screw-receiving apertures 22 of mounting plate members 20 connected to the main body 12, the mechanical fasteners being driven through the tissue and into the bone. The arch bar 11 comprises a front side 15 and a rear side 16, the term "front" or its variations as used herein referring to the side of an element facing away from the tissue, while the term "rear" or its variations as used herein refers to the opposing side, the side of an element facing or abutting the tissue, when the MMF device 10 is mounted onto the patient. The facing edge 14 of the arch bar 11 shall refer to the edge of the arch bar 11 that faces or is directed toward the opposing MMF device 10 when the MMF devices are mounted onto the patient. Wire retention projection members 17, such as hooks, buttons or the like, extend from the main body 12 of the arch bar 11 at laterally spaced locations. For a wire retention projection member 17 comprising a J-shaped hook that extends beyond the facing edge 14, as shown in the drawings, the free end of the hook 17 extends in the direction opposite that of the facing edge 14, which would be the superior direction for an arch bar 11 mounted on the maxilla and which would be the inferior direction for an arch bar 11 mounted on the mandible. In this manner, for an MMF device 10 affixed to the maxilla, the facing edge 14 will extend toward the mandible while the free ends of the hooks 17 will extend away from the mandible. For an MMF device 10 affixed to the mandible, the facing edge 14 will extend toward the maxilla while the free ends of the hooks 17 will extend away from the maxilla. A wire wrapped around a hook 17 on the mandibular MMF device 10 and around a hook 17 on the maxillary MMF device 10 when drawn tight and secured will prevent separation of the mandible from the maxilla.

A plurality of spaced tab members, teeth, anchors or the like 18 (referred to hereinafter collectively as "tabs" or "tab members"), bounded by gaps, spaces, notches or the like 19 (referred to hereinafter collectively as "gaps") are distributed laterally along the facing edge 14 of the arch bar main body 12, the term "lateral" or its variations as used herein referring to the longitudinal direction along the arch bar main body 12. The tab members 18 are preferably evenly spaced and equally sized, and preferably have a substantially square or rectangular configuration with beveled or rounded corners and parallel lateral sides. The gaps 19 are preferably equally spaced and sized, and have a substantially square or rectangular configuration with parallel lateral sides. The location of the tab members 19 determines the possible fixation locations for the mounting plates 20 along the arch bar 11.

The MMF device 10 further comprises a plurality of mounting plate members 20, each mounting plate member 20 comprising a main body 21, a screw-receiving aperture 22 disposed in the main body 21, and a coupling portion 25 extending from the main body 11 and sized and structured to encircle or retain a portion of the main body 12 of the arch bar 11, the coupling portion 25 extending over the front side 15, the facing edge 14 and the rear side 16 of the arch bar main body 12. The shape of main body 21 is variable, and several possible configurations are illustrated. Preferably, the configuration of all mounting plate members 20 are the same for a given MMF device 10. The main bodies 21 are preferably relatively wide and extend to the arch bar 11 so that bending, arching or other distortion of the mounting plate member main body 21 is precluded. The mounting plate member 20 possesses a front side 23, the side facing away from the tissue when the MMF device 10 is affixed to the patient, and a rear side 24, the side of the mounting plate member 20 facing or abutting the tissue. The screw-receiving apertures 22 may be provided with a beveled edge to better receive a screw head.

The coupling portion 25 of the mounting plate member 20 extends from the main body 21 in the direction away from the screw-receiving aperture 22 and comprises a curved mid-section 26 and an end 27, the coupling portion 25 being generally U-shaped in transverse cross-section and is configured and dimensioned to tightly receive the arch bar main body 11 with a highly limited range of movement in the front or rear direction. The end 27 preferably abuts the front side 23 of the mounting plate member main body 21. The end 27 may be affixed to the main body 21, such as by welding, bonding or like methods, or may be unsecured to the main body 21, in which case the coupling portion 25 of the mounting plate members 20 may be formed from a relatively rigid material that is resiliently bendable in a limited elastic manner to define a clip, such that the mounting plate members 20 may be snapped on or removed from the arch bar 11 without having to cut or sever the mounting plate member 20.

A slot or similar opening 28 is disposed in the curved midsection 26 of the coupling portion 25 and defines a pair of leg segments 29. The slot 28 of the curved midsection 26 is sized to have a lateral dimension greater than the lateral dimension of the tab members 18. In this manner, an arch bar tab member 18 may be positioned in the slot, 28 the leg segments 29 of the curved midsection 26 then fitting into the arch bar gaps 19 located to either side of the tab member 18.

Figure 4:
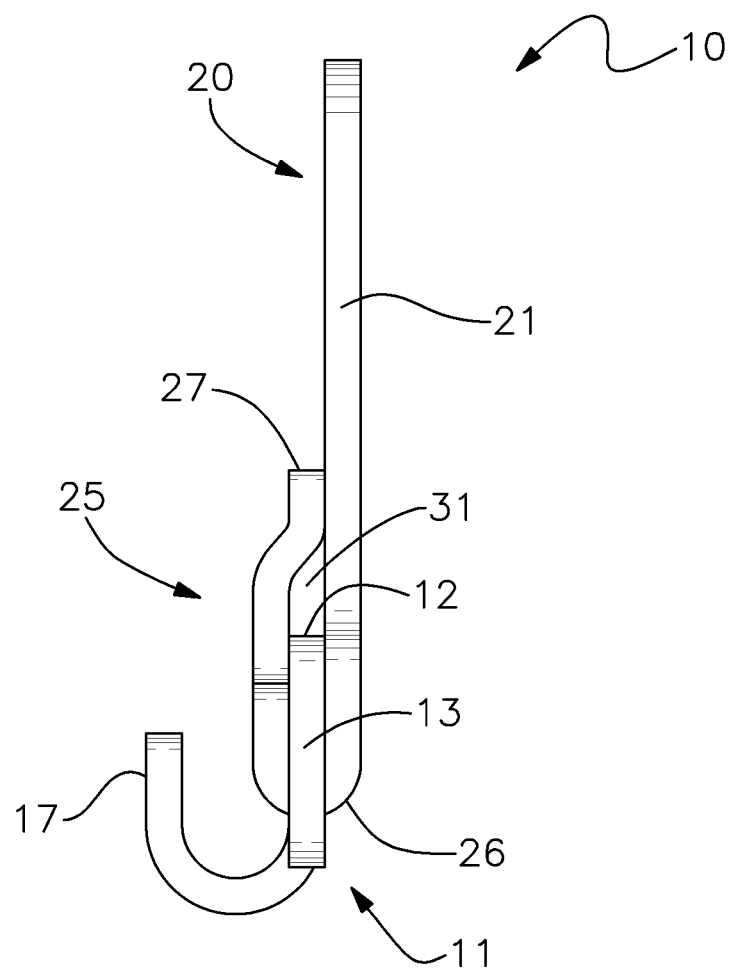
FIG. 4 is an end view of the embodiment of FIG. 1.
Figure 5:
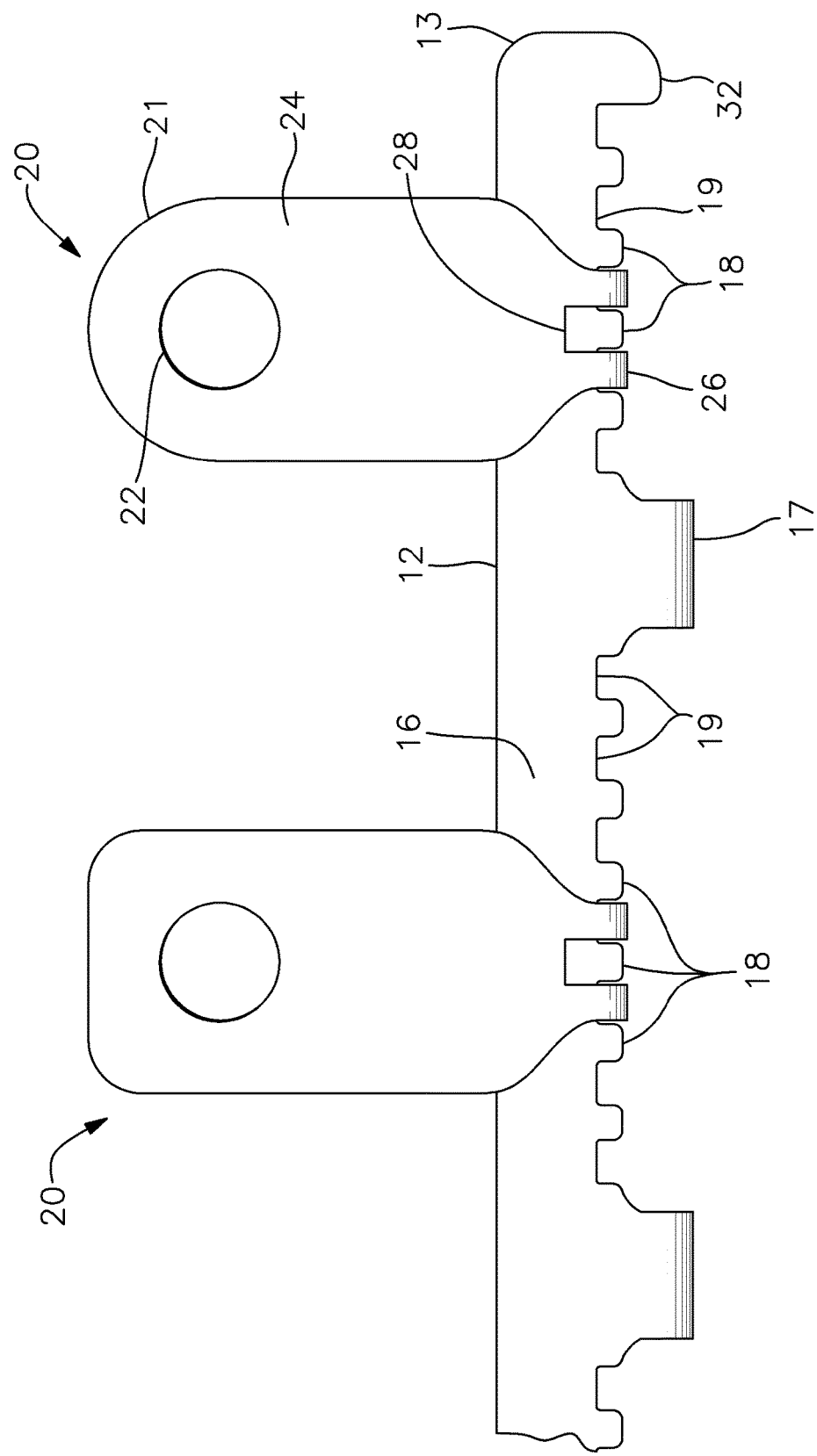
FIG. 5 is a partial rear view of the embodiment of FIG. 1.
Figure 6:
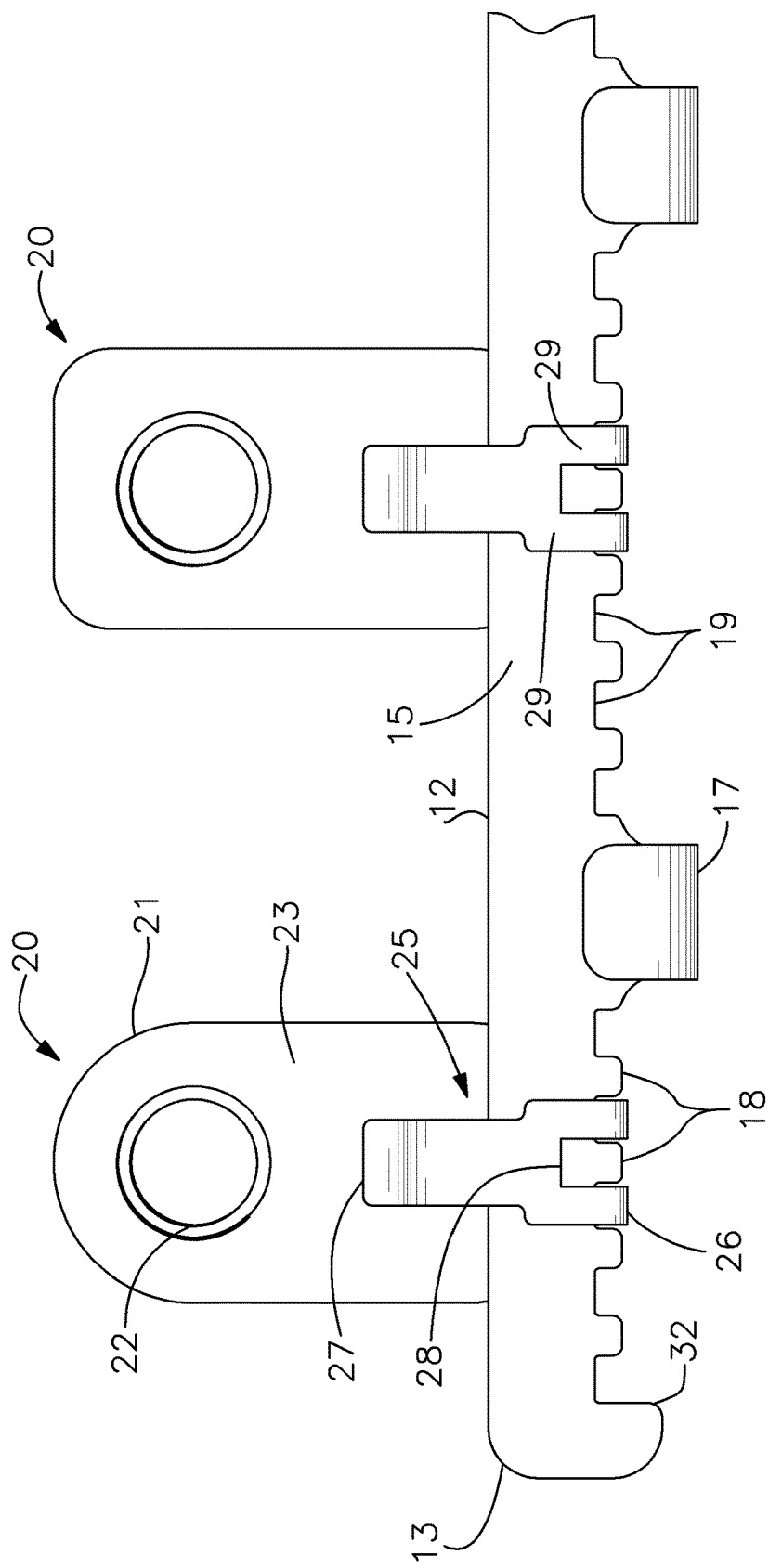
FIG. 6 is a partial front view of the embodiment of FIG. 1.

The length of the coupling portion 25, as shown best in FIG. 4, is chosen such that an interior open area 31 is created that is of greater length or dimension in the superior/inferior direction than the superior/inferior length or dimension of the arch bar main body 12, as measured at a point on the arch bar main body 12 that includes a tab member 18. With this structure the mounting plate member 20 may be shifted in the direction of the facing edge 14 of the arch bar main body 12, i.e., in the inferior direction for a maxillary MMF device 10 and in the superior direction for a mandibular MMF device 10, such that the leg segments 29 of the curved midsection 26 are moved beyond the tab member 18, i.e., no portion of the leg segments 29 remains in the arch bar gaps 19. This allows the mounting plate member 20 to be moved laterally along the arch bar main body 12, since the leg segments 29 pass below or above the tab members 18. When the desired location is determined, the mounting plate member 20 is shifted in the opposite direction, i.e., in the direction away from the facing edge 14, such that the curved midsection 26 seats on the chosen tab member 18, the leg segments 29 now residing in the adjacent gaps 19. In this manner, the mounting plate members 20 may be repositioned along the arch bar 11 so that the screw-receiving apertures 22 are not positioned over the roots of a tooth when the MMF device 10 is attached to the patient.

Alternatively described, each of the mounting plate members 20 occupies a first or mated position relative to the arch bar main body 12 wherein the coupling portion 25 is mated or coupled in fixed manner to the arch bar main body 12, the leg segments 29 enclosing a tab member 18, each leg segment 29 seated in adjoining gaps 19, and each leg segment 29 bounded by an outwardly situated tab member 18 such that lateral movement along the arch bar main body 12 is precluded. Each mounting plate member 20 may be shifted to occupy a second or free position relative to the arch bar main body 12 wherein the coupling portion 25 is not mated or coupled in fixed manner to the arch bar main body 12, but is instead able to move laterally along the arch bar main body 12. This lateral movement is enabled because in the free position the mounting plate member 20 is shifted in the direction toward the facing edge 14 of the arch bar main body 12, the size and configuration of the coupling portion open area 31 being sufficient such that the leg segments 29 of the coupling portion are moved beyond the tab members 18.

The wire retention projection members 17 divide the arch bar main body 12 into segments, whereby the lateral movement of a mounting plate member 20 is limited by adjoining wire retention projection members 17. In the preferred embodiment as shown in the drawings, for each segment defined by adjoining wire retention projection members 17 there is a single mounting plate member 20. Alternatively, however, a segment defined by adjoining wire retention projection members 17 may include multiple or no mounting plate members 20.

Preferably the main body 12 is provided with a pair of extended end stop members 32 that retain the outermost mounting plate members 20 on the main body 12 of the arch bar 11, the end stop members 32 being of greater length than the tab members 18 so as to be sufficient in length to block lateral movement of the leg segments 29 of the outermost mounting plate members 20 even when the mounting plate member 20 is shifted in the superior or inferior direction for repositioning on a different tab member 18.

Preferably, the tab members 18 and gaps 19 of the arch bar 11 and the slots 28 and leg segments 29 of the mounting plate members 20 are sized such that in-plane angular or lateral movement is precluded or restricted between the mounting plate members 20 and the arch bar 11 when a tab member 18 is received in a slot 28 and the leg segments 29 are positioned in adjoining gaps 19. In other words, the width of a slot 28 is only slightly greater than the width of a tab member 18, and the width of each gap 19 is only slightly greater than the width of the leg segment 29 of the curved midsection 26 to either side of the slot 28. This structure provides a secure fixation or fitted relationship between the mounting plate members 20 and the arch bar 11, whereby angular, sliding or pivoting movement of a mounting plate member 20 in the lateral direction on the arch bar main body 12 is precluded or extremely limited.

Another way to describe the relationship is that the tab member 18 is mated with the slot 28 and the two leg segments 29 are mated with the gaps 19 adjoining the tab member 18, with the near side of each of the tab members 18 situated outwardly from the adjoining gaps 19 acting in conjunction with the middle tab member 18 located in the slot 28 restricting movement of the leg segments 29 in the in-plane angular or lateral direction on the arch bar main body 12. Thus, the combination of three adjacent tap members 18 restrict or preclude movement of a mounting plate member 20 having its leg segments 29 fitted or mated in the gaps 19 in the in-plane angular or lateral direction relative to the arch bar main body 12.

A first embodiment of the MMF device 10 is illustrated in FIGS. 1 through 6. In this embodiment, the main body 21 of the mounting plate member 20 tapers at the area of transition to the coupling portion 25, such that the slot 28 and the leg segments 29 each have a constant width in the lateral direction (which corresponds to the longitudinal direction of the arch bar main body 12). The front of the coupling portion 25 extending to the end 27 is therefore narrower in width than the width of the main body.

In a second embodiment for the mounting plate member 20, as shown in FIGS. 7 through 10, the slot 28 laterally broadens in the direction toward the screw-receiving aperture 22 such that the leg segments 29 defined by the slot 28 extend farther in the direction toward the screw-receiving aperture 22. In this manner the main body 21 of the mounting plate member 20 transitions directly into leg segments 29 of the coupling portion 25.

Figure 7:
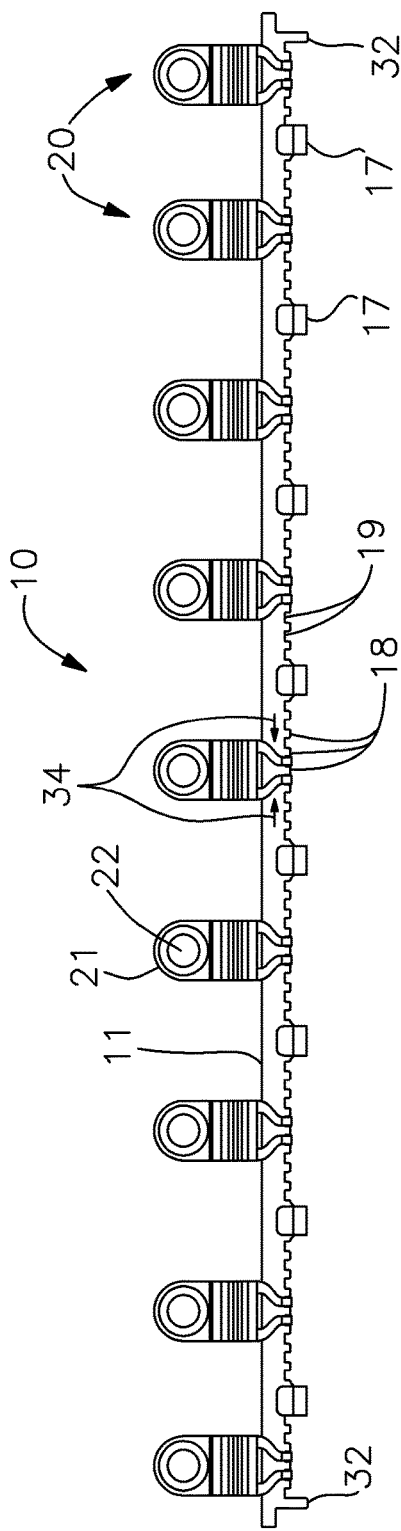
FIG. 7 is a front view of an alternative embodiment of the invention, shown as oriented for attachment to the maxilla.
Figure 8:
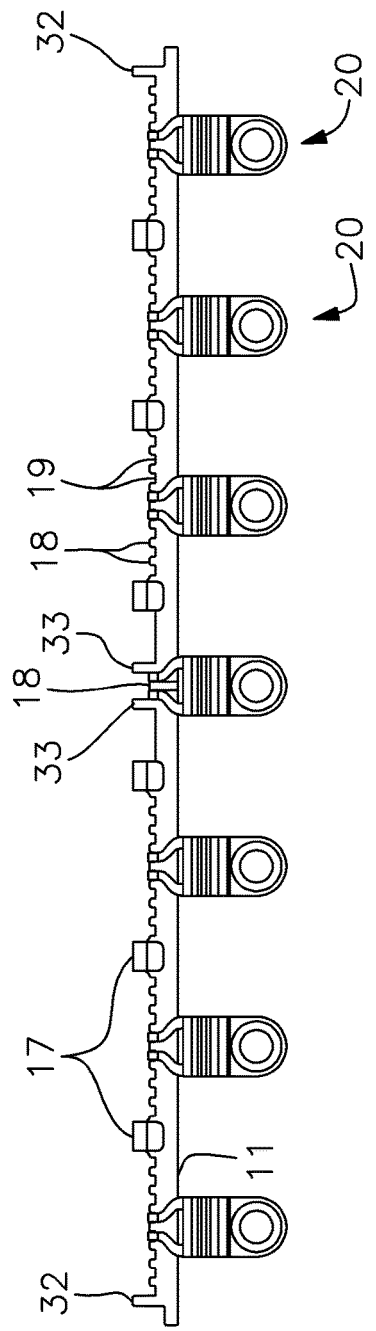
FIG. 8 is a front view of another alternative embodiment of the invention, shown as inverted from the earlier views as oriented for attachment to the mandible.
Figure 9:
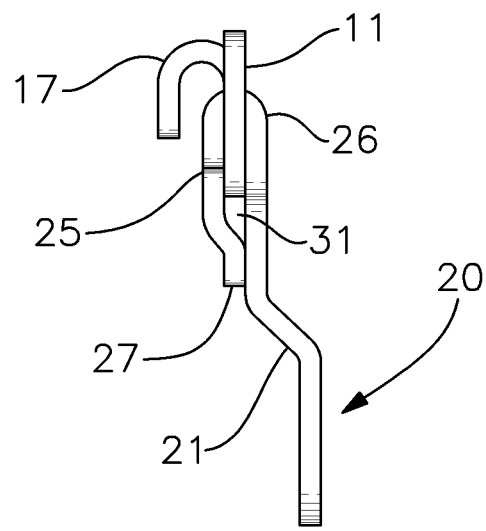
FIG. 9 is an end view of the embodiment of FIG. 8.
Figure 10:
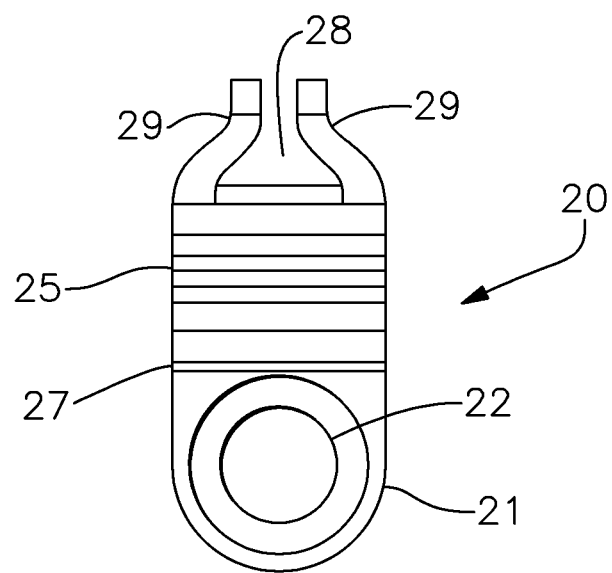
FIG. 10 is a front view of the mounting plate member illustrated in FIGS. 7 and 8.

FIG. 7 illustrates an embodiment of the MMF device 10 which is provided with a midline indicator or indicators 34, in this case shown as a pair of arrows inscribed or printed on the main body 12 of the arch bar 11. In this embodiment, the mounting plate member 20 positioned at the midline is movable laterally onto any of the tab members 18 positioned between the adjacent wire receiving projection members 17 as required to provide the proper location for safe insertion of the bone screw through the screw-receiving aperture 22. In the alternative embodiment shown in FIG. 8, the midline is defined by a pair of midline stop members 33. The midline stop members 33 are separated by two gaps 19 and one central tab member 18, with the midline stop members 33 being of greater length than said central tab member 18, such that the central mounting plate member 20 is restricted from lateral shifting.

To perform the procedure, the surgeon chooses an appropriately sized arch bar 11 or cuts a standard size arch bar 11 to the proper length, then bends the arch bar 11 as necessary to the desired curvature to match the curvature of the patient's mandible or maxilla. The patient's midline is determined and the arch bar 11 is contoured around the maxilla or mandible. The midline mounting plate member 20 is then affixed to the patient by passing a bone screw through the screw-receiving aperture 22 of the midline mounting plate member 20. The remaining mounting plate members 20 are now shifted or slid laterally along the arch bar 11 to the desired position to avoid damage to the tooth roots, and bone screws are passed through the screw-receiving apertures 22 into the tissue and bone of the patient, thereby affixing the MMF device 10 in position. The same procedure is then followed to attach the second MMF device 10 to the patient. Interconnecting wires or similar members are then passed from one MMF device 10 to the other MMF device 10, the wires being affixed to the wire retention projections 17, such that the MMF devices 10 may be brought together and the patient's lower and upper jaws are secured and affixed together in the closed position. Should the jaw need to be opened rapidly, the wires are easily cut. Complete removal of the MMF devices 10 is accomplished by backing out the bone screws.

It is understood that equivalents and substitutions for certain elements set forth above may be obvious to those of skill in the art, and therefore the true scope and definition of the invention is to be as set forth in the following claims.

We claim:

1. A maxillomandibular fixation device comprising:
    an arch bar comprising an elongated arch bar main body having a facing edge, tab members spaced along said facing edge, said tab members separated by gaps, and wire retention projection members positioned on said arch bar main body, wherein a plurality of said tab members and a plurality of said gaps are located between said wire retention projection members;
    mounting plate members disposed on said arch bar main body, said mounting plate members comprising a mounting plate main body, a screw-receiving aperture disposed in said main body, and a coupling portion, wherein said mounting plate members are laterally movable along said arch bar main body;
    said coupling portion comprising a curved midsection, a slot disposed in said curved midsection, said slot defining two leg segments, an end and an open area, wherein said coupling portion is adapted to receive said arch body main body within said open area;
    wherein each of said mounting plate members is adapted to be positioned on said arch bar main body at one of multiple positions between adjacent wire retention projection members such that one of said plurality of tab members located between said wire retention projection members is received within said slot of said mounting plate member and such that said leg segments of said mounting plate member are received within adjacent gaps of said plurality of said gaps located between said wire retention projection members;

wherein a length of said open area of said coupling portion in a inferior or superior direction is greater than the length in the inferior or superior direction of said arch bar main body at a point containing one of said tab members, such that with said mounting plate members shifted in a direction of said main body facing edge the leg segments are positioned beyond said gaps, such that said mounting plate members are movable laterally along said arch bar main body.

2. The device of claim 1, wherein said tab members, said slots, said leg segments, and said gaps are sized such that angular or lateral in-plane movement of said mounting plate members relative to said arch bar main body is precluded when said coupling portions of said mounting plate members are mated with said tab members and gaps.

3. The device of claim 1, wherein said tab members comprise sides and are substantially rectangular in configuration such that said sides are parallel.

4. The device of claim 1, wherein said slot has a constant width in a lateral direction.

5. The device of claim 1, wherein said end of said coupling portion is affixed to said main body of said mounting plate member.

6. The device of claim 1, wherein said end of said coupling member is not affixed to said main body of said mounting plate member.

7. The device of claim 1, further comprising a central tab member and two gaps bounded by a pair of midline stop members, said midline stop members being of greater length than said central tab member, such that lateral movement of one of said mounting plate members disposed between said midline stop members is precluded.

8. The device of claim 1, wherein said arch bar further comprises end stop members, said end stop members being of greater length than said tab members such that said mounting plate members are retained on said arch bar main body.

9. A maxillomandibular fixation device comprising:

an arch bar comprising an elongated arch bar main body having a facing edge, tab members spaced along said facing edge, said tab members separated by gaps, and wire retention projection members positioned on said arch bar main body;

mounting plate members disposed on said arch bar main body, said mounting plate members comprising a mounting plate main body, a screw-receiving aperture disposed in said main body, and a coupling portion, said coupling portion comprising a curved midsection, a slot disposed in said curved midsection, said slot defining two leg segments, an end and an open area;

wherein each of said mounting plate members is adapted to occupy a mated position relative to said arch bar main body, wherein one of said tab members is received within a slot of a mounting plate member and such that each of said leg segments of said coupling portion is received within one of said gaps adjacent said tab member received within said slot and bounded by another of said tab members, such that lateral movement of said mounting plate member relative to said arch bar main body is precluded;

and wherein each of said mounting plate members is adapted to alternatively occupy a free position relative to said arch bar main body, wherein lateral movement of said mounting plate member relative to said arch bar main body is not precluded, said mounting plate member being shifted in the direction of said facing edge such that said leg segments are removed from said gaps.

10. The device of claim 9, wherein a length of said open area of said coupling portion in a inferior or superior direction is greater than a length in the inferior or superior direction of said arch bar main body at a point containing one of said tab members.

11. The device of claim 9, wherein said tab members, said slots, said leg segments, and said gaps are sized such that angular or lateral in-plane movement of said mounting plate members relative to said arch bar main body is precluded when said coupling portions of said mounting plane members are mated with said tab members and gaps.

12. The device of claim 9, wherein said tab members comprise sides and are substantially rectangular in configuration such that said sides are parallel.

13. The device of claim 9, wherein said slot has a constant width in a lateral direction.

14. The device of claim 9, wherein said end of said coupling portion is affixed to said main body of said mounting plate member.

15. The device of claim 9, wherein said end of said coupling member is not affixed to said main body of said mounting plate member.

16. The device of claim 9, further comprising a central tab member and two gaps bounded by a pair of midline stop members, said midline stop members being of greater length than said central tab member, such that lateral movement of one of said mounting plate members disposed between said midline stop members is precluded.

17. The device of claim 9, wherein said arch bar further comprises end stop members, said end stop members being of greater length than said tab members such that said mounting plate members are retained on said arch bar main body.

* * * * *